United States Patent [19]

Kleinhappl et al.

[11] Patent Number: 5,032,361
[45] Date of Patent: * Jul. 16, 1991

[54] FEEDING DEVICE FOR INTRODUCING LIQUID OR GASEOUS SAMPLES

[75] Inventors: Erich Kleinhappl; Hermann Marsoner; Fritz Fischer, all of Graz, Austria

[73] Assignee: AVL AG, Schaffhausen, Switzerland

[*] Notice: The portion of the term of this patent subsequent to May 20, 2007 has been disclaimed.

[21] Appl. No.: 529,705

[22] Filed: May 30, 1990

Related U.S. Application Data

[63] Continuation of Ser. No. 213,154, Jun. 29, 1988, abandoned.

[30] Foreign Application Priority Data

Jul. 6, 1987 [AT] Austria .................. 1696/87

[51] Int. Cl.[5] .......................................... G01N 35/00
[52] U.S. Cl. ........................................ 422/67; 422/63; 422/64
[58] Field of Search ..................... 422/63-67, 422/81, 83, 102, 104, 50; 141/130, 270, 279, 284, 363; 73/864.21, 864.24, 864.25, 864.31, 864.73, 864.74, 863.01

[56] References Cited

U.S. PATENT DOCUMENTS

| | | | |
|---|---|---|---|
| 3,187,786 | 6/1965 | Hrdina | 141/130 |
| 4,264,327 | 4/1981 | Blum | 422/81 |
| 4,268,479 | 5/1981 | Webster | 422/68 |
| 4,499,053 | 2/1985 | Jones | 422/68 |
| 4,512,953 | 4/1985 | Marsoner et al. | 422/67 |
| 4,570,495 | 2/1986 | Terada | 73/864.25 |
| 4,609,017 | 9/1986 | Coulter et al. | 141/1 |
| 4,705,667 | 11/1987 | Marsoner et al. | 422/68 |
| 4,713,974 | 12/1987 | Stone | 73/864.23 |
| 4,720,463 | 1/1988 | Farber et al. | 435/291 |
| 4,798,705 | 1/1989 | Jakubowicz et al. | 422/63 |
| 4,927,603 | 5/1990 | Fischer et al. | 422/63 |

FOREIGN PATENT DOCUMENTS

377366 3/1985 Austria .
381794 11/1986 Austria .
2065169 1/1979 Fed. Rep. of Germany .

*Primary Examiner*—Robert J. Warden
*Assistant Examiner*—D. John Griffith, Jr.
*Attorney, Agent, or Firm*—Watson, Cole, Grindle & Watson

[57] ABSTRACT

A feeding device with a feeder element for liquid or gaseous samples includes an automatic sample exchanger having sample vessels for the liquid or gaseous samples and openings between the sample vessels through which the feeder element is automatically shifted from the feed position for serial samples to an initial position in contact with a feed opening for calibrating or cleansing media.

4 Claims, 4 Drawing Sheets

FEEDING DEVICE FOR INTRODUCING LIQUID OR GASEOUS SAMPLES

This application is a continuation, of application Ser. No. 213,154, filed June 29, 1988, now abandoned.

BACKGROUND OF THE INVENTION

This invention relates to a feeding device for introducing liquid or gaseous samples into an analysis path of an analysis apparatus, comprising a feeder element which may be brought from an initial position into one or more sample feed positions defining a direction of motion, the feeding device comprising an automatic sample exchanger for introducing serial samples, carrying the liquid or gaseous samples and taking them to the feeder element, moving during this process normal to the noted direction of motion.

DESCRIPTION OF THE PRIOR ART

A feeding device of the above kind is disclosed in German Laid Open No. 20 65 169. This known device is provided with a sample exchanger consisting of disks with openings, which cooperates with means of a feeder element shifted between a feed position and an initial position. This design is marked by the drawback that the device has no means accepting single samples. Besides, the device has another drawback resulting from its design. It is impossible or difficult to clean the feeding device between dippings, which means that the individual samples may influence one another.

Another feeding device is known from Austrian Pat. No. 381 794. This device comprises a feeder element which is tilted from an initial position into a feed position for single samples and is configured as a hollow needle positioned by a lever mechanism, which, in its initial position, cooperates with a funnel-shaped feed opening. Since the reference or cleansing media, as well as a quantitiy of air that may be required for drying the sample path, may enter through the feed opening into the feeder element during its initial position, a very simple configuration of the analyzing apparatus is achieved where no valves or other shut-off devices are necessary in the path of analysis to be travelled by the sample once it has passed the feed opening. Only for sample intake must the sealing contact between feeder element and funnel-shaped feed opening must be broken and the feeder element be tilted into a sample intake position; in all other operational states of the analyzing apparatus the media path between the individual feeder vessels and the waste vessel is fixed and closed, the medium actually entering into the path of analysis being controlled via three valves only.

The only disadvantage of the above feeding device is the relatively complicated lever mechanism, which is operated manually, taking the feeder element from initial to feed position, and which will not permit serial samples to be fed in automatically, unless considerable design efforts are made.

Another analyzing apparatus is described in Austrian-Patent No. 377 366, comprising a feeding device which has feeder elements for both single samples and serial samples. Since this design has two feeder elements, instead of one single element for all media to be entered, and since the paths of the individual media towards the analysis path in the analyzing apparatus are different in length, the conditions of measurement also are different, leading to measurement errors in addition to a complicated design.

SUMMARY OF THE INVENTION

Based on a feeding device for liquid and gaseous samples of the type referred to above, it is the main object of this invention to propose a feeding device which will permit the feeding of single samples in addition to that of serial samples in an uncomplicated design.

In the invention this object is achieved by providing the sample exchanger with openings between sample vessels, for the liquid or gaseous samples, through which openings the feeder element is automatically shifted from the feed position for serial samples to the initial position, coming into contact with the feed opening, for calibrating or cleansing media and by providing a further feed position for single samples. The vessels of the sample exchanger may be arranged either linearly or circularly. The opening behind each vessel, for instance a bore or a slot, will enable the feeder element to be moved to a position in which calibrating and cleansing media are entered, following a translatory or rotatory motion of the sample exchanger.

The desired sequence of motions is established, for instance, by fastening the feeder element onto a driven chain guided by a guide pulley, by which chain the feeder element can be lifted, parallel to the axis of the feed opening, from the initial position into a feed position for serial samples. The point where the feeder element is fastened to the chain is still below the guide pulley. If the chain moves on the feeder element is tilted into a feed position for single samples as soon as the fastening point arrives at the pulley.

Other sequences of motion of the feeder element are also practicable, provided they are automated and will return to an initial position for picking up calibrating and cleansing media via an opening in the sample exchanger.

In a preferred variant of the invention the sample exchanger is provided with a sample plate, which is driven from a stepping motor, if necessary, via a worm gear, and which has an alternating order of sample vessels and openings along its circumference, through which openings the feeder element will enter the feed opening. The sample plate can either be screw-fastened to the sample exchanger or it can be attached by means of a magnet.

In a further development of the invention a device for position monitoring is provided, by which the sample number of each vessel can be assigned to the corresponding measurement result, the noted position monitoring device being provided with Hall sensors located on the housing of the sample exchanger, which cooperate with a magnet on the sample plate. Monitoring of the position of the sample plate, which may be put on its support in various positions, or rather, monitoring of the position of a particular sample, is achieved by means of a Hall sensor and a permanent magnet attached to the sample plate, but could also be contrived in other ways, for example, by electro-optical devices. For the exact positioning of the feeder element relative to each sample of the sample exchanger, the axle of the sample plate carries a slotted disk, which is in contact with a photoelectric barrier that may be configured as a fork. The stepping motor is processor-controlled via the signals of this device.

For better maintenance and care of the feeding device a further development of the invention provides that the sample exchanger be removably fastened to the housing of the feeding device via a coupling carrying a stop lever, and that the feeder element, preferably a hollow needle, be centered relative to the axis of the sample vessel.

Finally it is proposed by the invention that an electronic control and monitoring unit be provided for processing the signals from the position monitoring device of the sample exchanger and for control of the stepping motor of the sample plate as well as of the feeder element, if required, which control and monitoring unit should be located under the sample plate in the housing for better protection. This will ensure a fully automated sample feed for both serial samples and single samples, operation being restricted to the input of YES-NO decisions via a key panel.

DESCRIPTION OF THE DRAWINGS

Following is a more detailed description of variants of the invention, as illustrated by the accompanying drawings, in which.

DETAILED DESCRIPTION OF THE PREFERRED EMBODIMENTS

Figure 1:
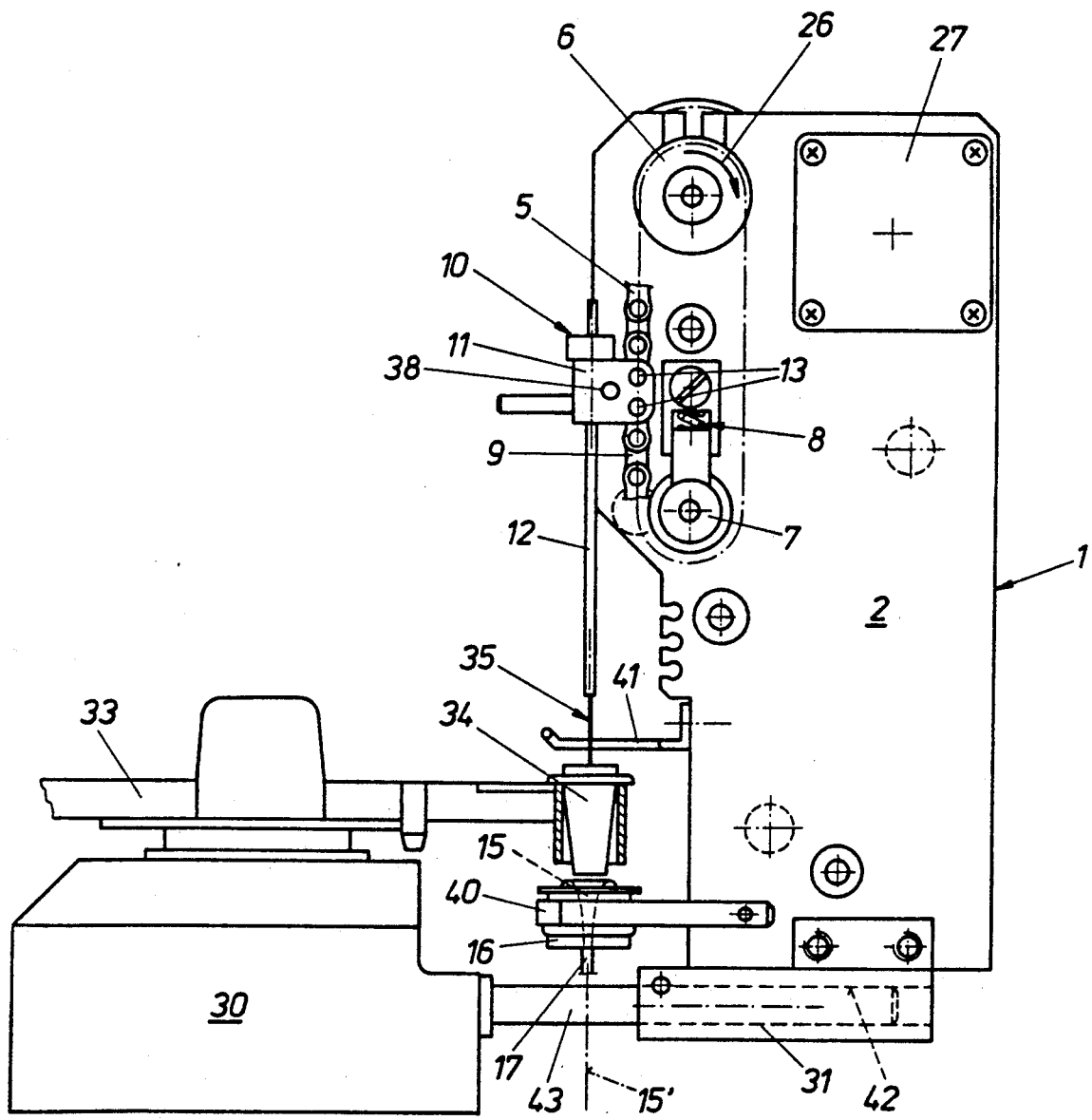
FIG. 1 presents a side view of a feeding device according to the invention.
Figure 2:
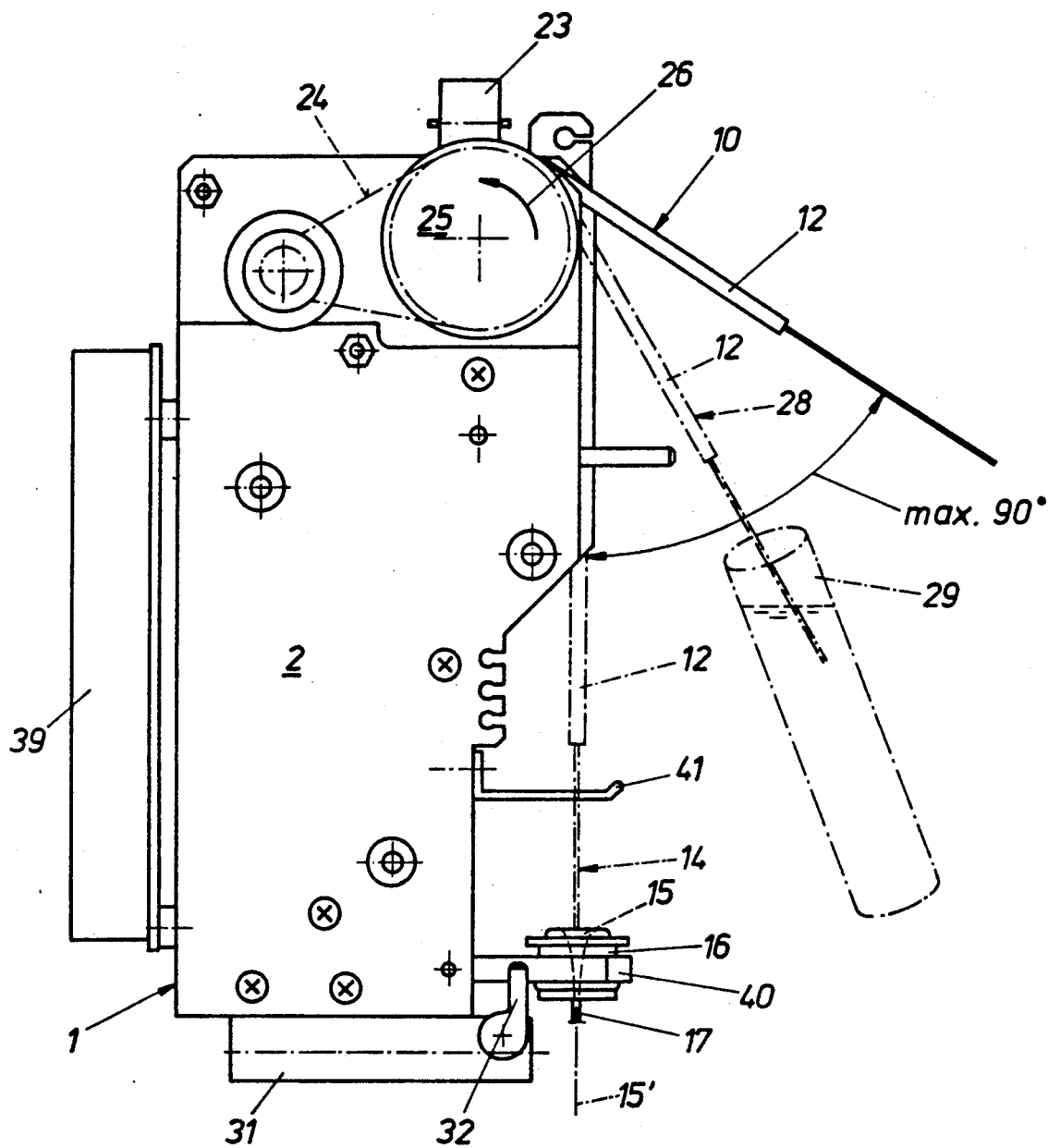
FIG. 2 shows another side view, the sample exchanger having been removed.

The variant of a feeding device 1 presented in FIGS. 1 and 2 has a housing 2 in which a driven belt 5 is guided by a guide pulley 6 and the pulley 7 of the chain tightener 8. The belt 5, which is driven via the guide pulley 6, is configured as a chain 9 to which is attached the feeder unit 10 comprising a needle holder 11 and a hollow needle 12 screwed onto the holder, the needle holder 11 is fastened to the chain 9 by means of chain pins 13 guided in a slotted part of the housing 2, for instance by grooves (not shown here). In the initial position 14 the hollow needle 12 of the feeder element 10 is in sealing contact with the feed opening 15 of a funnel element 16, on whose side opposite of the feed opening 15 the calibrating and cleansing media are entered via the feed pipe 17 in a manner already described in Austrian-Patent No. 381,794, via valves of a valve unit located in front of the feeder element 10 in the direction of flow of the media. The hollow needle 12 is connected to a flexible tube leading to the analysis path (not shown here) of an analyzing apparatus via an optical sensor 23.

The chain 9, which is driven by a stepping motor 27 via a belt 24 and a pulley 25 in the direction of arrow 26, will lift the hollow needle 12 of the feeder element 10 from the initial position 14, at first parallel to the axis 15' of the feed opening 15, subsequent to which the needle holder 11 will eventually reach the guide pulley 6, by which it is moved through a sector of a circular path, such that the hollow needle is tilted out of the housing 2 into a feed position 28 for single samples. The tilting range limited by a stop is 90°. In the feed position 28 for single samples the feeder element 10 may be fed with samples from any kind of vessel 29 desired.

An automatic sample exchanger 30 is centered and arrested in position by a coupling 31 with a stop lever 32 via bolts 43 of the sample exchanger 30 that are inserted into bores 42 of the housing 2 of the feeding device. The sample plate 33 of the sample exchanger 30, which carries vessels 34 containing the test samples along its circumference, extends into the path of the hollow needle 12 in the area between funnel element 16, or rather, its support 40, and a needle protector 41 located on the housing, such that the hollow needle 12 can be dipped into the individual vessels 34 for sample intake, parallel to the axis 15' of the feed opening 15. During this process the feeder element 10 is in the feed position 35 for serial samples.

The feeding device 1 further is provided with a position control element made up of Hall sensors for example (not shown here), which are cooperate with a magnet 38 on the feeder element 10, for instance on the needle holder 11 of the hollow needle 12. In addition, an electronic control and monitoring unit 39 is provided for control of the stepping motor 27 and processing of the signals from the position control element.

Figure 3:
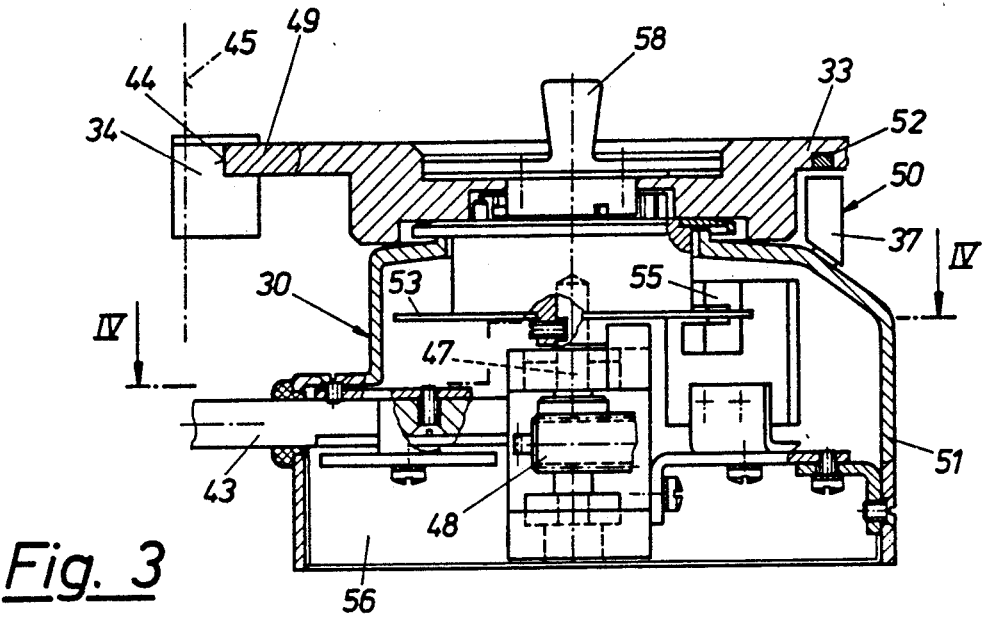
FIGS. 3 and 4 give a detailed view of the sample exchanger of the feeding device, partly cut along lines III—III and IV—IV in FIGS. 3 and 4.
Figure 4:
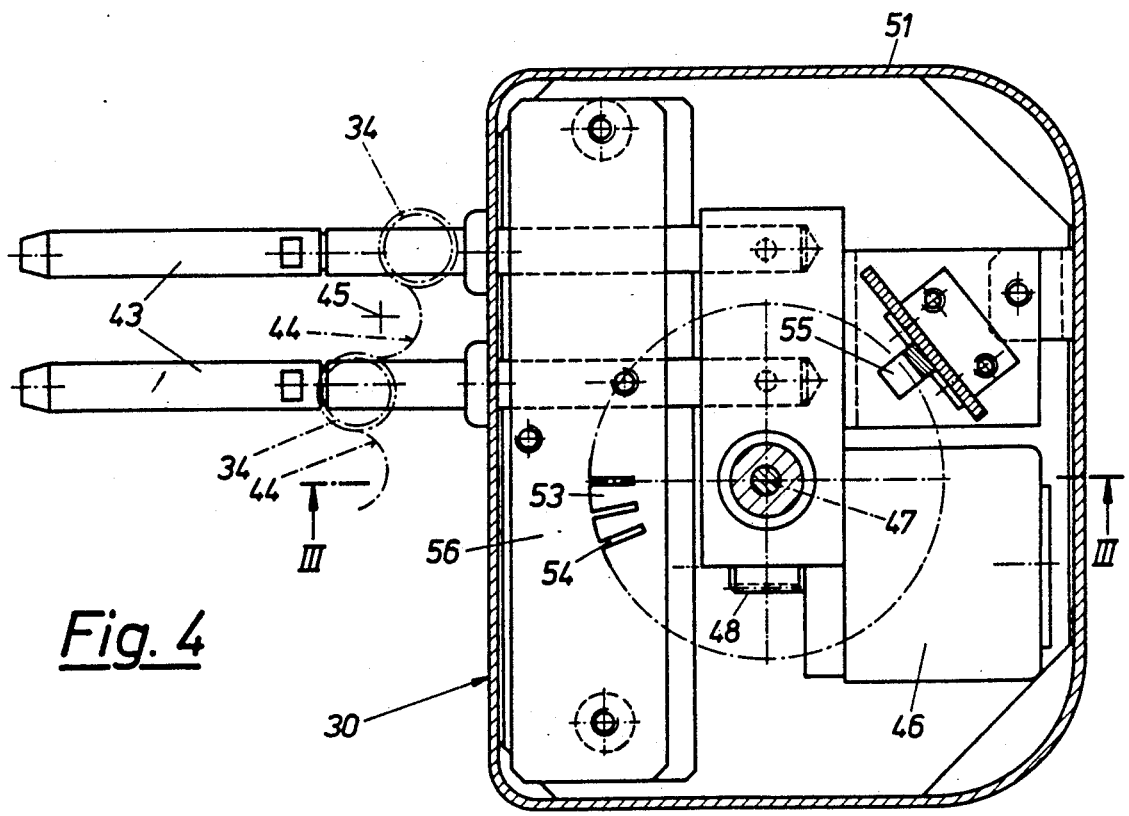

FIGS. 3 and 4 give a detailed view of the sample exchanger 30, the positions of the vessels 34 of the sample plate 33 placed outside of the cutting plane being indicated by dash-dotted lines in FIG. 4. The openings 44 between the individual vessels 34, which are placed along the circumference 49 of the sample plate 33, are clearly visible, through which openings the feeder element (indicated here by line 45) will return to the initial position 14 (FIG. 2) from the feed position 35 for serial samples shown in FIG. 1.

The sample plate 33 together with its axle 47 is driven from a stepping motor 46 via a self-locking worm gear 48, which will take the individual samples in the vessels 34 to a position beneath the hollow needle 12 of the feeder element 10.

Figure 6:
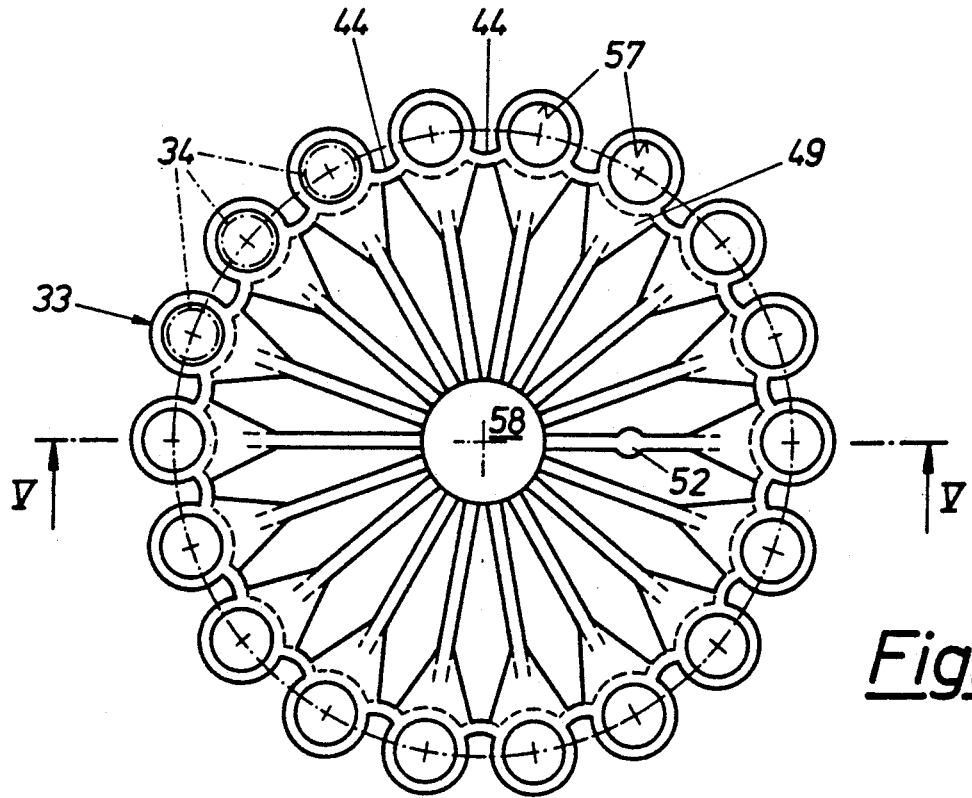

The sample exchanger 30 of the feeding device also is provided with a position monitoring device 50 comprising a Hall sensor 37 located on the housing 51 of the sample exchanger, and a magnet 52 attached to the sample plate 33, which magnet is also shown in FIG. 6. This device serves to determine the position of the sample plate 33 which may be put on the sample exchanger in various positions, and to assign the sample number of each vessel 34 to the corresponding test result of the analyzing apparatus following the feeding device. Accurate positioning of the sample plate 33 is done by means of a disk 53 permanently fastened to the axle 47, which disk 53 has slots 54 that are scanned by a photoelectric barrier, for example a fork barrier.

Via an electronic control and monitoring unit 56 the stepping motor 46 is processor-controlled by means of the signals from the position monitoring device 50. The unit 56 can also be used to control the feeder element 10, or rather, to coordinate the signals from the control and monitoring unit 39 for the feeder element 10.

In order to protect the control and monitoring unit 56 contained in the drive unit, the entire unit is covered and sealed against liquids by the housing 51.

The automatic sample exchanger 30 is configured as a separate unit that can be separated from the feeder element upon releasing the stop lever 32.

Figure 5:
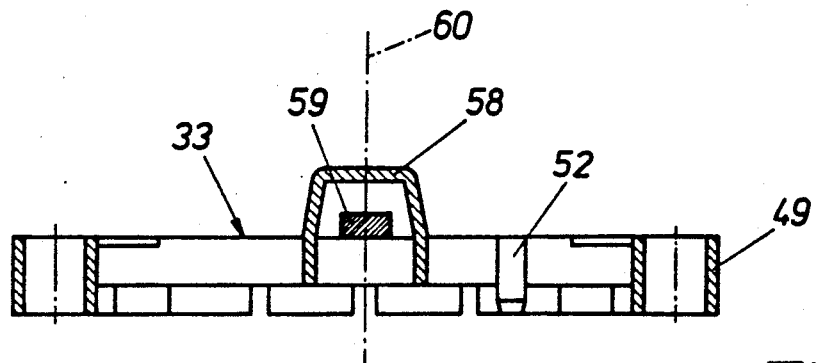
FIGS. 5 and 6 show a design variant of the sample exchanger in FIGS. 3 and 4.

FIGS. 5 and 6 show a sample plate 33 with eighteen bores 57 holding the sample vessels 34 and with openings 44 arranged in between. In the center of the sample plate, which may be a molded part of metal or plastic, there is a handling knob 58 for lifting and changing of the vessels 34. This handling knob 58 contains a magnet 59 fastening the sample plate 33 on the sample exchanger 30; the sample plate may also be fastened with screws or clips. The magnet 52 of the position monitoring device 50 is located at a distance of about half the plate radius from the axis 60 of the sample plate 33.

We claim:

1. A feeding device for introducing liquid or gaseous samples into an analysis path of an analyzing apparatus which comprises:

a stationary element having an opening into which calibrating or cleansing media can flow, said opening defining an axis perpendicular to said opening, a feeder element through which liquid or gaseous samples can flow into an analysis path of an analyzing apparatus, said feeder element comprising a needle holder and a hollow needle, an automatic sample exchanger which includes a rotatable sample plate mounting a plurality of serial sample vessels at a periphery thereof and defining recesses between said sample vessels, and a first stepping motor for rotating said sample plate, said sample exchanger being mounted so that said sample vessels and said recesses can be aligned with said axis, and drive means for said feeder element, said drive means comprising a guide pulley, a link chain which extends around said guide pulley, a second stepping motor for driving said link chain, and a first control means for controlling the operation of said second stepping motor, said link chain being connected to said needle holder such that movement of said link chain by said second stepping motor can cause said hollow needle to move (1) in a first direction along said axis and through a recess in said sample plate to an initial position within said opening of said stationary element, (2) in an opposite second direction along said axis and out of said opening and then in said first direction to a serial sample feed position in a serial sample vessel, and (3) in a third direction which is tilted with respect to said axis to a single sample feed position for receiving a single sample from a single sample vessel.

2. A feeding device according to claim 1, wherein said link chain, said guide pulley and said first control means are located in a second housing, wherein said sample exchanger is removably fastened to said second housing via a coupling carrying a stop lever, and wherein said hollow needle of said feeder element, when in said serial sample feed position, is centered relative to an axis of the sample vessel into which the hollow needle extends.

3. A feeding device according to claim 1, including a position-monitoring device for assigning a sample number of each of said sample vessels to a corresponding measurement result, said position-monitoring device being provided with Hall sensors located on said sample exchanger which cooperate with a magnet on said rotatable sample plate.

4. A feeding device according to claim 3, including a second control means for processing signals from said position-monitoring device and for controlling said first stepping motor and said first control means, said second control means being located under said sample plate and in a first housing.

* * * * *